United States Patent
Dayal

(10) Patent No.: US 7,295,695 B1
(45) Date of Patent: Nov. 13, 2007

(54) DEFECT DETECTION VIA MULTISCALE WAVELETS-BASED ALGORITHMS

(75) Inventor: Aditya Dayal, Sunnyvale, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 755 days.

(21) Appl. No.: 10/260,374

(22) Filed: Sep. 26, 2002

Related U.S. Application Data

(60) Provisional application No. 60/366,425, filed on Mar. 19, 2002.

(51) Int. Cl.
*G06K 9/00* (2006.01)
*G06K 9/36* (2006.01)

(52) U.S. Cl. ............. 382/145; 382/147; 382/149; 382/232

(58) Field of Classification Search ............. 382/141, 382/144, 145–152
See application file for complete search history.

(56) References Cited

U.S. PATENT DOCUMENTS

| | | | |
|---|---|---|---|
| 5,539,514 A * | 7/1996 | Shishido et al. | 356/237.4 |
| 6,163,619 A * | 12/2000 | Maruo | 382/141 |
| 6,259,960 B1 * | 7/2001 | Inokuchi | 700/110 |
| 6,584,236 B1 * | 6/2003 | Maruo et al. | 382/298 |
| 6,804,381 B2 * | 10/2004 | Pang et al. | 382/111 |
| 2002/0057831 A1 * | 5/2002 | Hiroi et al. | 382/149 |
| 2003/0063792 A1 * | 4/2003 | Hiroi et al. | 382/149 |

* cited by examiner

*Primary Examiner*—Brian Le
(74) *Attorney, Agent, or Firm*—Beyer Weaver LLP

(57) ABSTRACT

A method of detecting a defect in a reticle or wafer uses wavelet transforms to differentiate between real defects and pattern noise. A first image and a second image of a sample are aligned. A wavelet transform is obtained of the difference between the images. The wavelet transformed difference image is filtered to distinguish between real defects and pattern defects.

9 Claims, 12 Drawing Sheets

Amplitude

Amplitude

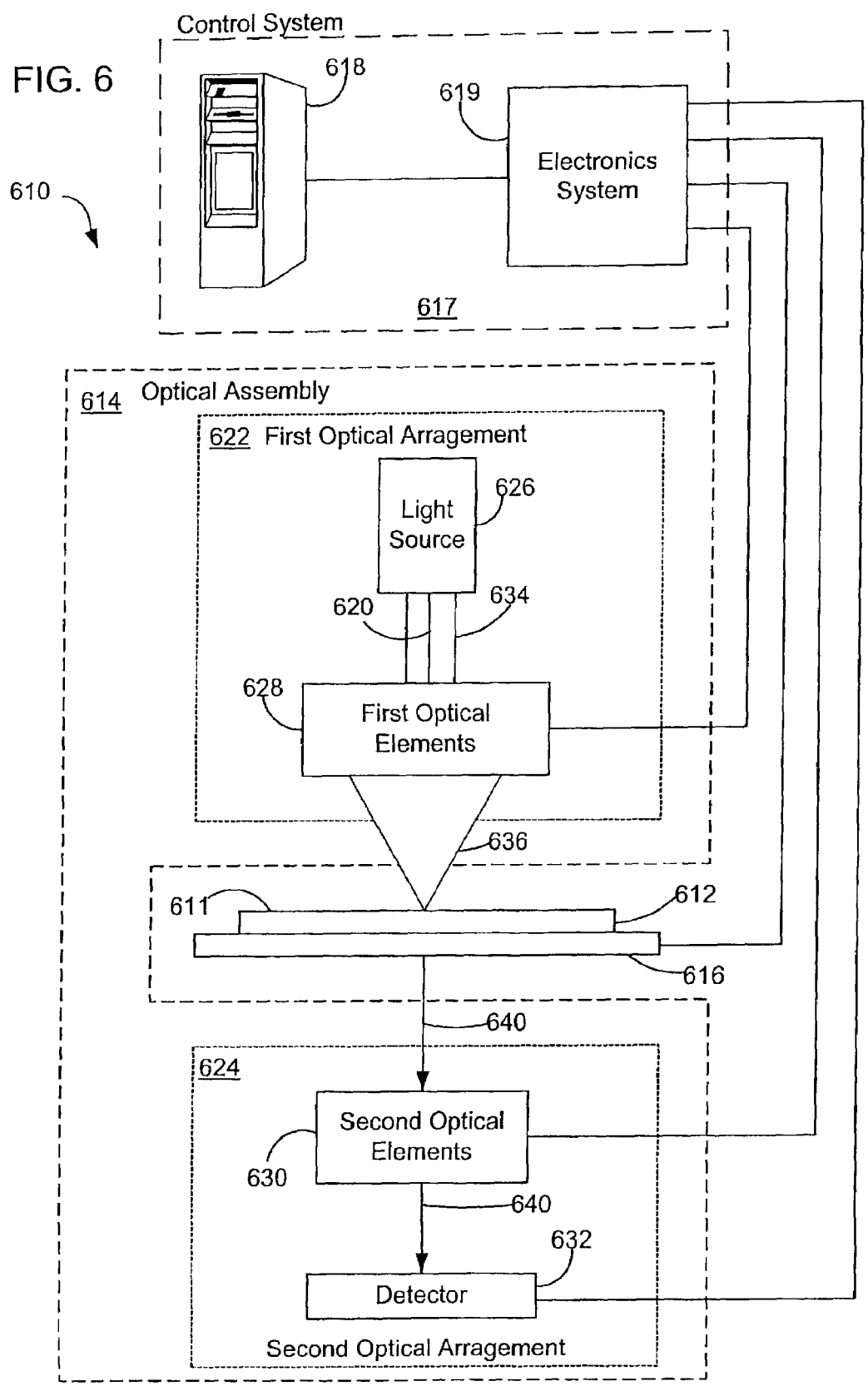

DEFECT DETECTION VIA MULTISCALE WAVELETS-BASED ALGORITHMS

CROSS REFERENCE TO RELATED PATENT APPLICATION

This application takes priority under U.S.C. 119(e) of U.S. Provisional Application No. 60/366,425 filed on Mar. 19, 2002 entitled "Defect Detection Via Multiscale Wavelets-Based Algorithms," by Aditya Dayal, which is incorporated by reference in its entirety for all purposes.

BACKGROUND OF THE INVENTION

The present invention relates generally to producing pattern defect inspection systems for wafers, masks, and reticles. More particularly, the present invention relates to a method of filtering optical images to improve the sensitivity to "real" defects on inspected samples.

In a conventional optical inspection system, defects are detected by subtracting a reference image from a test image and low-pass filtering the difference image. The test image is an optical image of an area on the photomask. The reference image may be an optical image of a similar area on an identical die or on the same die or a rendered design database. The grayscale residues, i.e., portions of the difference image having a value other than zero, represent defects in the inspected sample.

"Real" defects must be isolated from spurious or "false" defects. Conventional methods are susceptible to the generation of false defects since defects will be detected wherever the test image does not match the reference image. Thus, false defects will be detected whenever incomplete subtraction occurs and residues exceed a specified threshold. To minimize false defect occurrences, stringent requirements are imposed on the mechanical stability of the inspection tool. For example, high frequency vibrations must be minimized to prevent alignment mismatches which will result in numerous errors. The algorithms for aligning and filtering the test and reference images must ensure precise matches. Even rendered images may produce numerous false defects if the algorithm for matching the rendered image from the design database file is not strictly controlled. Rendering database reference images to match the test images are particularly difficult for low-$k_1$ reticles which are used in state-of-the-art optical lithography.

Filtering of the difference image is performed to increase the defect signal relative to the background residue, which would be zero if the images were identical. Conventional techniques perform low-pass filtering operation on the difference image to reduce the quantity of pattern noise, i.e., false defects arising from the factors discussed above. Low pass filtering has the effect of smoothing out the difference image. Defects are then determined as the grayscale residues exceeding a specified threshold. False defects counts may be reduced by raising the thresholds for defect detection, but raising the threshold may mask real defects.

More sophisticated filtering techniques are available to enhance the defect's signal to noise ratio relative to the background in the difference image. For example, Fourier transform techniques are useful for filtering out periodic (repeating) signals. However, defects in wafers and other samples may be embedded in a background that is non-stationary, i.e., one whose frequency is not constant. In such cases Fourier transform methods have limited utility. Many kinds of background patterns may be observed on masks, for example, including stationary or non-stationary types. They may be non-repeating. What is needed is a mechanism for improving the signal from a defect relative to various types of background noise in the detection of defects on photomasks, reticles, or wafers.

SUMMARY OF THE INVENTION

To achieve the foregoing, and in accordance with the purpose of the present invention, methods and systems for defect detection using multi-scale wavelets-based algorithms are described.

One embodiment of the present invention provides a method for detecting defects in a reticle or photomask or wafer. A first image of a portion of a wafer or reticle and a second image of a portion of a wafer or reticle is obtained. A wavelet transform of the difference between the first image and the second image is generated. The transformed image is filtered and an inverse transform performed on the filtered image. Defects are then identified from the inverse transformed image.

In another embodiment, at least one of the first or second images, or a difference image derived from them, is decomposed using a Daubechies 4 basis function to obtain a wavelet transform. Filtering the transformed image comprises selecting one or more coefficients to represent a defect signal. In other embodiments, filtering the wavelet transformed image comprises identifying a portion of the transformed image coefficients within a predefined range and modifying the values of the coefficients.

These and other features and advantages of the present invention will be presented in more detail in the following specification of the invention and the accompanying figures, which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which:

FIG. 6 is a diagrammatic representation of an inspection system in accordance with one embodiment of the present invention.

DETAILED DESCRIPTION OF SPECIFIC EMBODIMENTS

Figure 1:
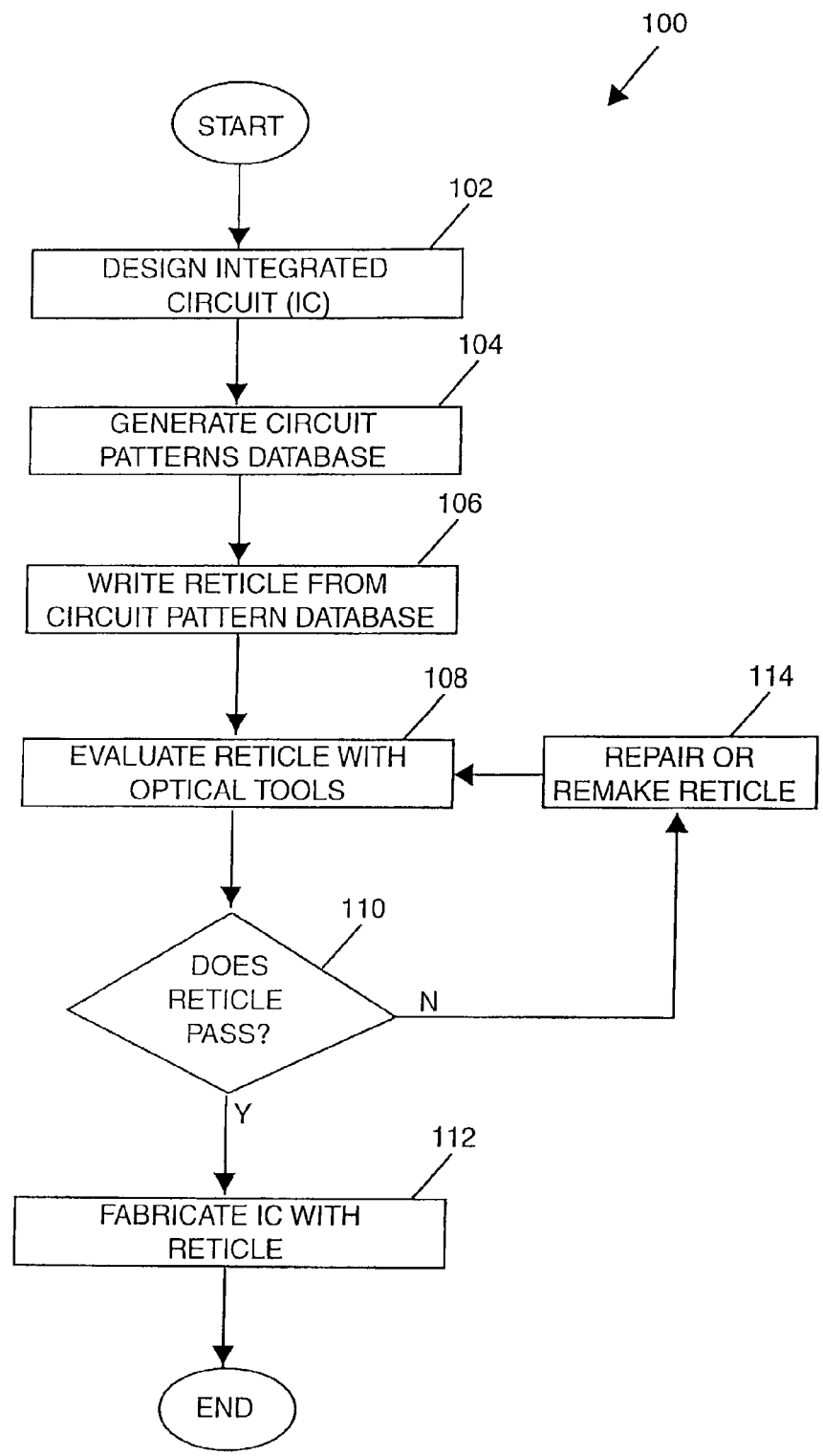
FIG. 1 is a flowchart illustrating an integrated circuit design process in accordance with one embodiment of the present invention.

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Any signal such as a signal representing the image of an inspected reticle, wafer, or sample may be expressed or decomposed into basic functions. The decomposed signal may be processed to better identify real defects.

Conventionally, the image signal is a time-domain (or space-domain) signal. The intensity (e.g. brightness) of the image is measured as a function of time, such as occurs when an optical or electrical beam is scanned sequentially across a reticle or wafer in a controlled pattern known as a raster scan. The collected scan data may be used to generate an image of the sample. Alternatively, a complete image of a sample may be obtained using optical equipment, converting the optical image to an electrical representation by any of several methods well known in the art, such as through the use of an array of charge-coupled devices (CCD's). The outputs from the CCD's produce typically an electronic representation of a two-dimensional image. A typical image is in a rectangular shape, each indivisible portion of the image represented by a pixel (picture element). For example, a picture may be described as 256×256 pixels, i.e., 256 pixels in width and 256 pixels in height. The intensity of the pixel is often expressed in digital form as a grayscale image, with a black pixel typically representing a value of 0 and a bright white pixel representing a value of 255 on a grayscale-256 system. Various intensities of gray represent intermediate values from 1 to 254, increasing in intensity in linear fashion from dark gray to near white. The image array is thus a representation of a signal (intensity) at each spatial point in the array.

Methods are also known in the art for generating entire images from electron beam inspection methods. The present invention is intended to apply to all images of samples, no matter how generated, and whether or not the images are in electronic representation format.

Decomposition of the image may be helpful in distinguishing defects in the signals from noise. For example, using a Fourier transform, a signal may be expressed as the sum of a series of sines and cosines. The Fourier transform provides only frequency resolution but no time resolution. Thus, using the Fourier transform, a signal may be decomposed into all of the frequencies present but the transformed signal would not isolate when in time (or where in the space comprising an image) those frequencies occurred. Samples of difference images with embedded defects comprise defects which are non-stationary, i.e. do not form repeating patterns. The Fourier transform is of limited utility in filtering noise or other defects which appear in only some portions of the image. Even using the Fast Fourier transform, the defect will be buried in the noise because the defect extends throughout Fourier space. The Fourier transform of a "spike-like" (sharp) defect extends over a wide range of frequencies. It is not localized in the frequency domain. Thus, if a range of frequencies is filtered out, part of the defect may be lost also. Thus, to recover a "spike" type defect, all of the Fourier coefficients may be necessary. For this reason, Fourier transforms are unsuitable for isolating defects from background frequencies present on inspected masks, reticles, or wafers.

In order to better identify real defects, especially subtle defects, in the presence of stationary and non-stationary background patterns, such as may be found on masks, reticles, and wafers, techniques of the present invention include decomposing the image signal into joint time (space) and frequency representations using a wavelet transform. For example, the wavelet transform of a sharp "spike-like" defect is usually represented by a very small number of coefficients. If these coefficients can be determined, then they can be preserved but the rest of the coefficients representing the background can be zeroed out before inverse transforming. In order to perform a wavelet transform, a fully scalable window is shifted along the signal. For every position the frequency spectrum is calculated. Each time the process is repeated, a slightly longer or shorter window may be used for every new cycle. As a result, the original signal may be decomposed into a collection of time frequency (or space-spatial frequency) representations, all with different resolutions and thus providing a multi-resolution analysis. Wavelet transforms decompose the signal into space-scale representations, where different scales represent information at different spatial frequencies. For example, as illustrated in FIG. 3B, level 1 coefficients represent the highest spatial frequency content, level 2 coefficients represent the next highest frequency contents, and so on. The decomposed signal (i.e., after performing a wavelet transform) is filtered to remove pattern noise. An inverse transform is performed and the defects identified by setting a threshold level. Difference signals are transformed using wavelets in one embodiment of the present invention. In other embodiments, a target signal (e.g. from a tested wafer) and a corresponding reference signal are transformed separately using wavelets, and the transformed target signal is then subtracted from the transformed reference signal to obtain a difference signal. Filtering using wavelet transforms, as practiced in embodiments of the present invention enables generation of a resultant image with higher signal-to-noise ratios and thus facilitates identification of defects, whether by manual or automatic techniques.

FIG. 1 is a flowchart illustrating an integrated circuit design process 100 used to identify defects wafers, masks, and reticles in accordance with one embodiment of the present invention. Initially, in operation 102, an integrated circuit (IC) device is designed using any suitable design techniques. For example, an IC designer may use preexisting schematic library blocks to form the IC device using, for example, electronic design automation (EDA) tools. In some cases, the IC designer may create the IC device or part of the IC device from scratch with the aid of any suitable design system, such as conventional computer aided design (CAD) tools. For example, the IC designer may use a schematic CAD tool to plan the logic diagrams for a particular IC device. Still further, the IC designer may write a description of the IC device or portions of the IC device with the aid of a hardware design language, such as VHDL.

Next, in operation 104 the IC designer generates a circuit pattern database (commonly referred to as a "layout") from the IC design in operation 104. The circuit pattern database is composed of a plurality of electronic representations of layout patterns for IC layers that are later converted into a plurality of reticles that are used to fabricate a plurality of physical layers of an IC device. Each physical layer of the fabricated IC device corresponds to one of the reticles and an associated one of the electronic representations of the circuit pattern database. For example, one electronic representation may correspond to a diffusion pattern on a silicon substrate, another to a gate oxide pattern, another to a gate polysilicon pattern, another to a contact pattern on an interlayer dielectric, another to a line pattern on a metallization layer, and so on. Each electronic representation is composed of a plurality of polygons or other shapes (herein, referred to as "figures"), which together define the reticles pattern.

The circuit pattern database may be generated using any suitable technique, for example, by using EDA or CAD tools. For example, the IC designer may manually lay out the circuit patterns for the IC device with or without pre-existing library cells. Alternatively, a synthesis tool may automatically create circuit patterns for the IC device from scratch or by piecing together preexisting library cells.

After the circuit pattern database is generated, the circuit pattern database is used to produce a plurality of reticles in operation 106. The reticles may be produced by any suitable pattern generator or reticle writer equipment, such as a MEBES" 4500, commercially available from ETEC of Hayward, Calif.

Each reticle corresponds to one or more electronic representation(s) from the circuit pattern database. A reticle is then inspected in operation 108, and it is determined whether the reticle passes inspection in operation 110. If the reticle passes inspection, the reticle may then be used to fabricate a physical layer of the IC device in operation 112. However, if the reticle does not pass inspection, the reticle is either repaired or remade in operation 114, and the new reticle is inspected in operation 108. Operations 106 through 112 may be implemented for some or all of the electronic representations of the circuit pattern database.

The present invention may be implemented on any suitable inspection tools. The inspection tool may be in the form of an optical inspection tool or an electron microscopy inspection tool. The inspection tool may be configured to inspect any type of sample, such as a reticle or wafer. For example, a KLA 301, 351, or 353UV Reticle Inspection Tool, commercially available from KLA-Tencor of San Jose, Calif., may be employed. One embodiment of an inspection system is described below in reference to FIG. 6.

Inspection of the reticle in operation 108 includes performing a wavelet transform on the difference signal or image obtained from the test image and the reference image. The wavelet transform may be performed using any of a series of basis functions known to those of skill in the art including but not limited to the Daubechies 4 wavelet. The wavelets derive from scaling and translating a single function, the mother wavelet, such as shown by the following equation:

$$\Psi_{s,t}(x) = \frac{1}{\sqrt{s}} \Psi((x-t)/s)$$

where $\Psi(x)$ is the mother wavelet, s represents a scaling factor and t represent a translating factor. The wavelet transform involves the decomposition of a signal into coefficients which completely describe the signal as a linear combination of wavelet functions. The continuous wavelet transform in one dimension is obtained by correlating the input signal with the wavelets at each scale and translation:

$$WTf(x)_{s,t} = C_{s,t} = \frac{1}{\sqrt{s}} * \int f(x) * \Psi_{s,t}(x) dx$$

The integration is repeated to obtain the wavelet coefficient at each s (scale) and t (time).

For the discrete case, in one embodiment, f is a vector with N observations and s, t are discrete samples (i, j) of a dyadic grid. The dyadic representation refers to the fact that in this embodiment wavelets are scaled by powers of two. In other embodiments, other scaling factors may be used to enable control of the resolution in different wavelet levels in accordance with the anticipated distribution of defects among various frequency ranges. Translation is performed by shifting along the axis by integer multiples of scale. The discrete wavelet transform is more appropriate for transforming signals in the real world, where signals have well known cut-off frequencies. In the discrete case, the wavelets are obtained from the mother wavelet at a specific number of scale and translations. When the scale is changed by powers of two and the translations are integer multiples of the scale, then we have a Dyadic discrete wavelet transform (dyadic DWT). The use of the discrete wavelet transform provide a practical solution which may be implemented on digital computers without undue processing time as compared to the continuous wavelet transform. The DWT allows for much faster calculations than the continuous wavelet transform (CWT). Existing algorithms for DWT's enable calculations with linear computational complexity, i.e. time~O(N) where N is the size of the input vector.

In one embodiment, a dyadic wavelet transform is performed at each step of the transform process. Each successive scaled version in a dyadic representation will have one half of the spectral frequency of the previous scale. For example, the dyadic DWT of an image with a width of 256 pixels will contain the highest frequency of 128/256 pixels$^{-1}$ in accordance with the Nyquist sampling criterion. According to the Nyquist criterion, at least 2 pixels are needed to sample (the shape of) any structure or geometry. Therefore, the smallest structure or cycle that one can hope to resolve is at least 2 pixels long. In other words, the highest spatial frequency sampled is 1/(2 pixels)=0.5 pixels$^{-1}$. Therefore, in a vector that is 256 long, we can have 128 measurements of the highest spatial frequency in the signal (which is 128/256 or 0.5 pixel$^{-1}$). Along the same lines, the sampling may produce 64 measurements of the spatial frequency 0.25 pixels$^{-1}$ (i.e., a signal that has a 4 pixel cycle), 32 measurements of an 8 pixel cycle (0.125 pixels$^{-1}$), and so on. In the example vector having 256 points, in scale 1 the wavelets are narrowest and they are translated each time by 2 pixels so as to give 128 samples (128 shifts). In scale 2, the wavelets are twice as broad as in scale 1, and are now translated by 4 pixels, to give 64 samples (64 shifts). In scale 3, the wavelets are 4 times as broad as in scale 1, and are translated by 8 pixels to give 32 samples. The process continues until the broadest wavelet desired is represented in a scale.

The wavelet transform decomposes a signal into wavelet coefficients. At each scale the magnitude of the wavelet coefficients represent the similarity of the original signal to the wavelets, across spatial position. Each intensity value in the scaled version is represented by a coefficient, with the spatial location of the frequencies within that band shown by their left to right position within the transformed level. Coefficients corresponding to the highest frequency band or wavelet level may be designated as level one coefficients, with coefficients corresponding to lower bands successively designated as level 2 coefficients, level 3 coefficients, etc.

The wavelet coefficients, $C_{i,j}$, determine the relative contribution of each wavelet in the signal. The signal may be reconstructed by summing over all of the translations at each scale in accordance with the following equation:

$$f(x) = \sum_{i=0}^{S} \sum_{j=0}^{T} C_{i,j} * \Psi_{i,j}(x)$$

To the extent that real defects may be localized to one or a small group of coefficients in the wavelet transforms (levels), processing may be performed on the remaining coefficients to attenuate or eliminate pattern noise before reconstruction of the signal. Thus, according to embodiments of the present invention, the signal to noise ratio in evaluating real defects may be enhanced.

Figure 2:
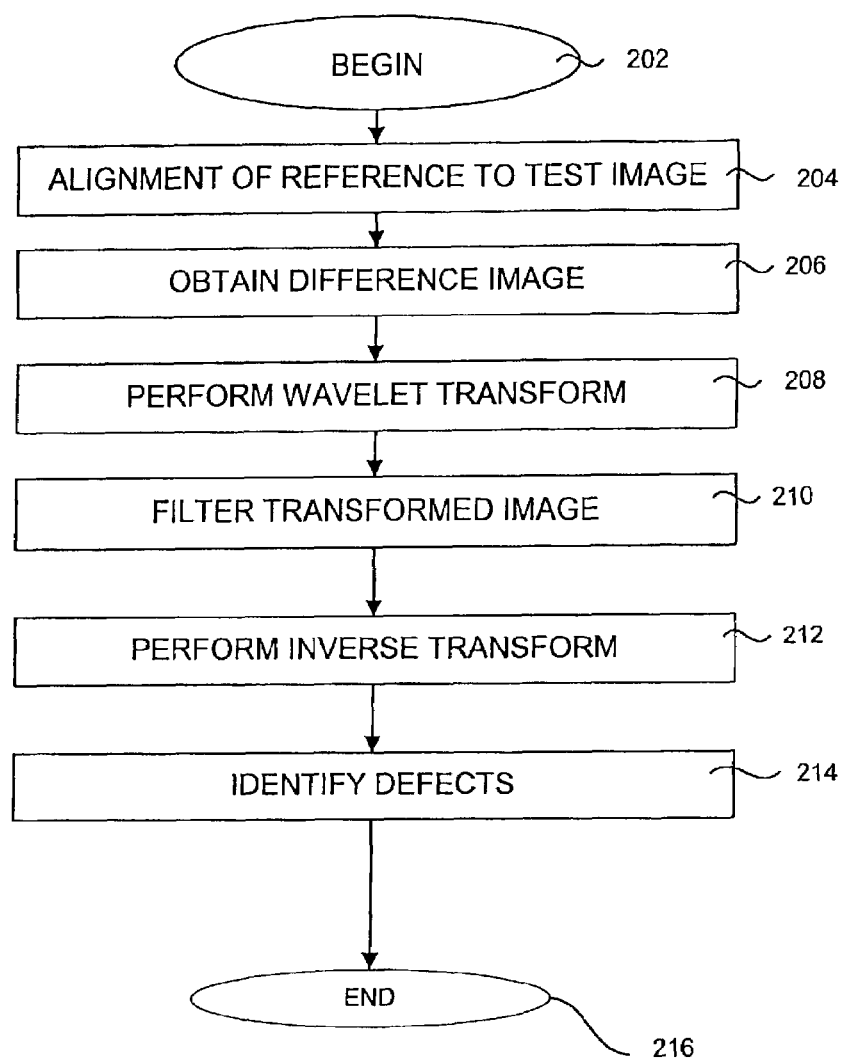
FIG. 2 is a flowchart illustrating an inspection of a sample in accordance with one embodiment of the present invention.

FIG. 2 is a flow chart illustrating an inspection of a sample in accordance with one embodiment of the present invention. For example, FIG. 2 is representative of an expansion of phase 108 as illustrated and identified with reference to FIG. 1. The process begins with alignment of the reference to the test image (204). The test image may be that of a reticle, mask with photo resist, or a wafer. The image of the sample is compared to a reference image which may be that of a similar portion of the pattern on the same wafer, an image taken from a second wafer and stored, or a rendered image from a design data base. Alignment may be performed conventionally in a variety of ways. For example, patterns can be registered to each other by minimizing residues (sum-square-error). Alternatively, patterns can first be shifted by integer pixels to maximize the cross-correlation coefficients. Then, for example, linear or parabolic interpolation might be used to determine sub-pixel shifts. Finally, the sub-pixel shifts can be applied to one of the pair of images using a standard interpolation algorithm.

In another embodiment of the present invention, alignment may be performed by executing wavelet transforms of each of the test image and the reference image. Then, one can match the same feature across different scales, and estimate the shifts between the features at each scale. Finally the shifts can be applied using a standard interpolation method such as bicubic.

The process then proceeds to obtain a difference image between the test image and the reference image (206). This phase may be performed by subtracting the values representative of one image from another. It is expected that residue gray scale values (i.e., intensity values for the difference image) will indicate a true defect or a pattern defect (i.e., noise). For example, where the reference image is identical to the test image the difference image may have values of 0 at those corresponding pixels. Noise may result from any of several sources, including misalignment between the test image and the reference image and high frequency vibrations induced into the measurement tools.

A two-dimensional electronic representation of the difference image may be subjected to a wavelet transform (208) using two-dimensional image processing techniques. For example, the two-dimensional image may be processed by performing a one-dimensional wavelet transform on each row to generate an intermediate image, followed by one-dimensional wavelet processing of the rows of the intermediate image. This example is illustrative of one of many techniques known in the art to form two-dimensional processing and is not intended to be limiting.

Wavelet transforms are linear operators. Therefore, in other embodiments, the wavelet transform may equivalently be taken of each of the reference and the test images and the transformed images subtracted to obtain the same result as taking the wavelet transform of the difference image.

Utilization of different wavelet families for the wavelet transform result in associated trade-offs between localization and smoothness. Accordingly, one or more wavelet families may be selected for transformation of the image based on the requirements of the particular application. Wavelet basis functions which better match a defect in shape provide a higher valued coefficient in wavelet space. In one embodiment of the present invention, the wavelet transformed image comprises a concatenation of individual wavelet levels, each providing a spatial representation identifying the location in the image where the spectral content selected for that wavelet level is located. Each of the wavelet levels comprises a group of coefficients that represents the intensity and location of the signals falling within the wavelet level's frequency band. Those wavelet levels having more coefficients provide better spatial resolution. The transformed image may then be filtered to eliminate those portions of the time and scale representation of the signal which are expected to contain pattern and/or random noise (210).

Real defects may be modeled in wavelet space by using relatively few of the coefficients generated in the wavelet transform, perhaps as few as a single coefficient where the wavelet basis function matches the defect characteristics well. In one embodiment, filtering in the wavelet space comprises discarding certain coefficients falling within a preselected range. Discarding may comprise setting the noise coefficients to zero or otherwise reducing their values relative to the coefficients. In one embodiment, the preselected range may involve setting a threshold level sufficiently high that most or all of the pattern or other spurious defects identifiable in the transformed image fall below the threshold yet all of the coefficients corresponding to the real defects fall above the threshold. The pattern noise will be subdued by setting the coefficients falling below the threshold to zero or otherwise reducing the values of the coefficients. In other embodiments, the difference image may yield a negative value for the "true" defects and the coefficient levels above a threshold are reduced or set to zero. The thresholds may be established empirically from samples of like wafers, reticles or masks with known defects. The examples given are intended to be illustrative and not limiting.

In other embodiments, filtering techniques may operate uniformly on entire wavelet coefficient levels. For example, where the defects to be identified may be characterized as "spike" type defects, these defects will often show up in the 2 rightmost wavelet coefficient levels (indicating higher spatial frequency). Thus, coefficients in all other wavelet coefficient levels, i.e., all "bands" to the left of the "bands" identifying the defect (i.e., all wavelet levels representing lower spatial frequencies) may be reduced or set to zero. Thus filtering may be selectively limited to 2 or 3 wavelet levels. Noise filtering techniques may also take advantage of generalized knowledge as to the position of defects or the absence of defects in portions of the sample. For example, where it is known that the right margin of a die has no defects, the entire right margin portion in each of the wavelet levels may be set to zero.

The above-described filtering techniques are intended to be illustrative and not limiting. Other techniques may be employed, and in particular in conjunction with knowledge as to the type of defects to be identified, in order to produce an efficient filtering scheme. Filtering involves setting the correct threshold or otherwise using an effective scheme to filter out the noise components but not the defects.

The next stage involves performing an inverse transform to reconstruct the original signal without the filtered components (212). The final stage involves identifying defects (214). The resultant differential image emphasizes the difference between the true defects and non-defective portions of the wafer, photomask, or reticle by eliminating the pattern noise in the previous steps. The operator may select thresholds so that signal portions falling outside a pre-determined range will be identified as true defects. As a result of the filtering steps performed on the coefficients in the wavelet transformed image, a higher defect signal to noise ratio will be present in the reconstructed image. In one embodiment, threshold setting occurs in the reconstructed image to identify the defects over the noise which had not been filtered out in the wavelet domain. Those signals following within the selected range, such as below a certain threshold, will be ignored. In this manner, it is expected that the threshold may more easily be established so that true defects are discernable from false or pattern defects.

Figure 3A:
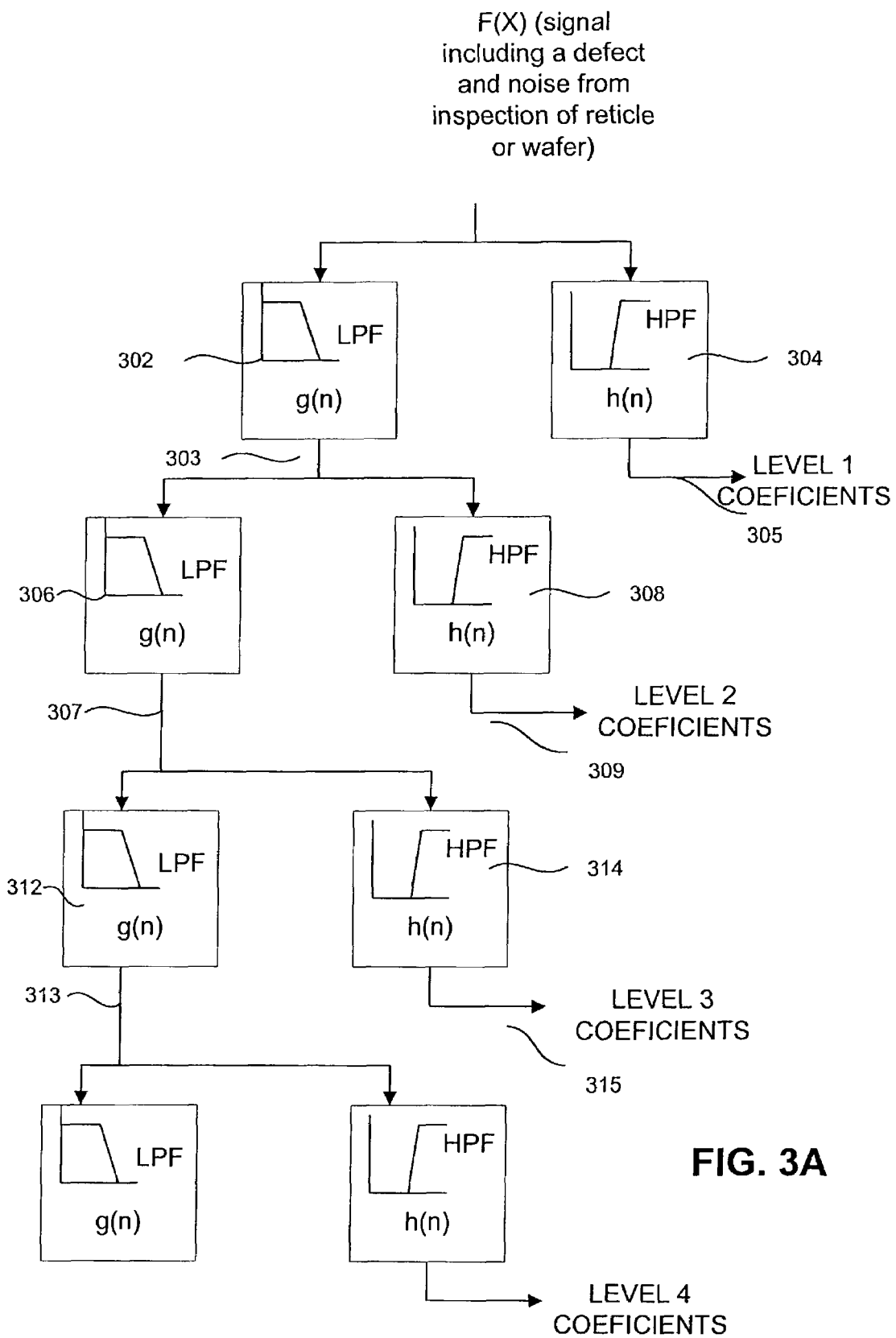
FIG. 3A is a diagrammatic representation illustrating the creation of scaling functions in accordance with one embodiment of the present invention.
Figure 3B:
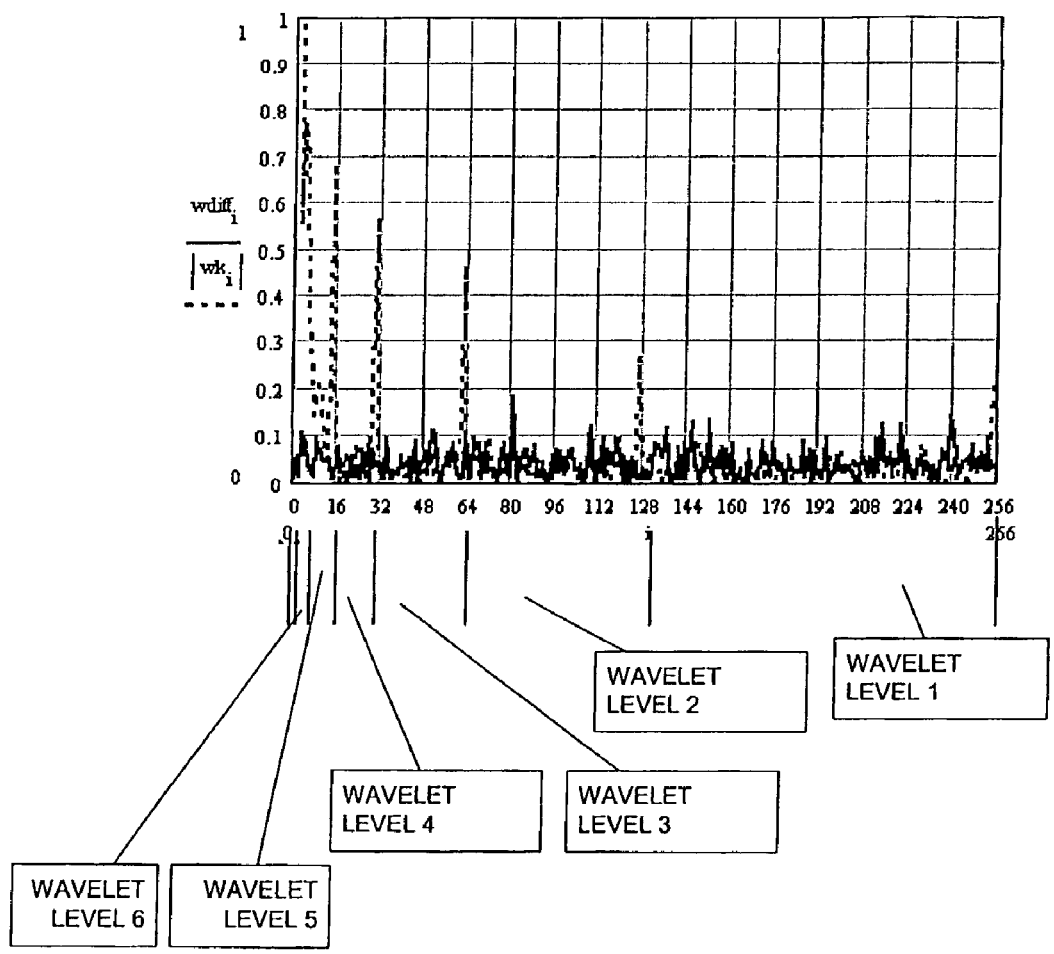
FIG. 3B is a diagrammatic representation illustrating the concatenation of wavelet levels in accordance with one embodiment of the present invention.

FIG. 3A is a diagrammatic representation illustrating the decomposition of an input signal F(x) (e.g., difference signal) into several spectral bands according to one embodiment. This diagram is an expansion of step 208 in FIG. 2, and illustrates the relative spatial frequencies of the various coefficient levels generated in one embodiment of the wavelet transform. Depicted is scaling using a power of 2 to form a dyadic wavelet transform. Each of the spectral bands is a wavelet, a scaled and shifted version of the mother wavelet. Each of the wavelets is a collection of coefficients ($C_{S,t}$). Through proper selection of the scaling and translation parameters (S,t), the original input signal F(x) may be processed by stages having the equivalents of a low pass and high pass digital filter, using the output of the high pass filter 304 to generate the level 1 coefficients 305 and the low pass filter output 303 for further filtering. The output 305 will represent only the upper half of the available frequency content and corresponds to the highest frequency band of the input signal F(x). The low pass filter output 303 is further filtered using a low pass filter 306 and a high pass filter 308, the high pass filter output 309 generating a second wavelet represented by the level 2 coefficients. Again the low pass filter output 307 from this stage of the filter is used for further filtering in subsequent stages. The output 315 of the high pass filter 314 in the next stage will generate another wavelet, represented as the level 3 coefficients. The output 313 from the low pass filter 312 is directed to further filtering in subsequent stages. The process continues until the desired numbers of wavelets (levels of coefficients) are generated.

In this embodiment, the original signal F(x) is decomposed into dyadic blocks (shifting and scaling based on powers of 2). As illustrated in FIG. 3B, the wavelets may be concatenated to represent the fully decomposed input signal. The wavelet transform offers superior temporal (spatial) resolution of the high frequency components and scale resolution (corresponding to frequency) of the low frequency components. That is, the low frequency components have a high degree of resolution as to frequency, but their spatial location (for the frequency band represented by the applicable wavelet level) is low. As shown, the highest frequency band such as level (segment) 1 (322) allocates 128 pixels to locate the position of the highest frequency components whereas the wavelet levels corresponding to lower wavelet levels, such as level 332 provide much poorer time (spatial) resolution (e.g. 8 pixels for level 322 corresponding to level 5 coefficients). Thus, the transformation of this embodiment will be better able to resolve higher frequencies in space (time) and lower frequencies in frequency (scale).

FIG. 3B illustrates various wavelet coefficient levels generated in a dyadic wavelet transform according to another embodiment. The wavelet level 1 coefficients represent the highest frequencies in the input signal F(x) and provide the best spatial resolution for the locations of the defect's having frequency components in the frequency bands represented in the wavelet level. In contrast, wavelet level 6 has very few coefficients and thus provides poor spatial resolution, i.e., with only 4 coefficients, the defect may at best be locatable within one-half or one-quarter of the image. The signal information corresponding to this wavelet level would have excellent frequency resolution (i.e., the bandwidth assigned to this wavelet level would be a fraction of the bandwidth assigned to level 1) and would represent low frequencies. Defects showing low frequency characteristics are typically not subtle defects, thus high spatial resolution for these defects is much less critical than for subtle defects that may more often appear in the first several wavelet coefficient levels.

Figure 3C:
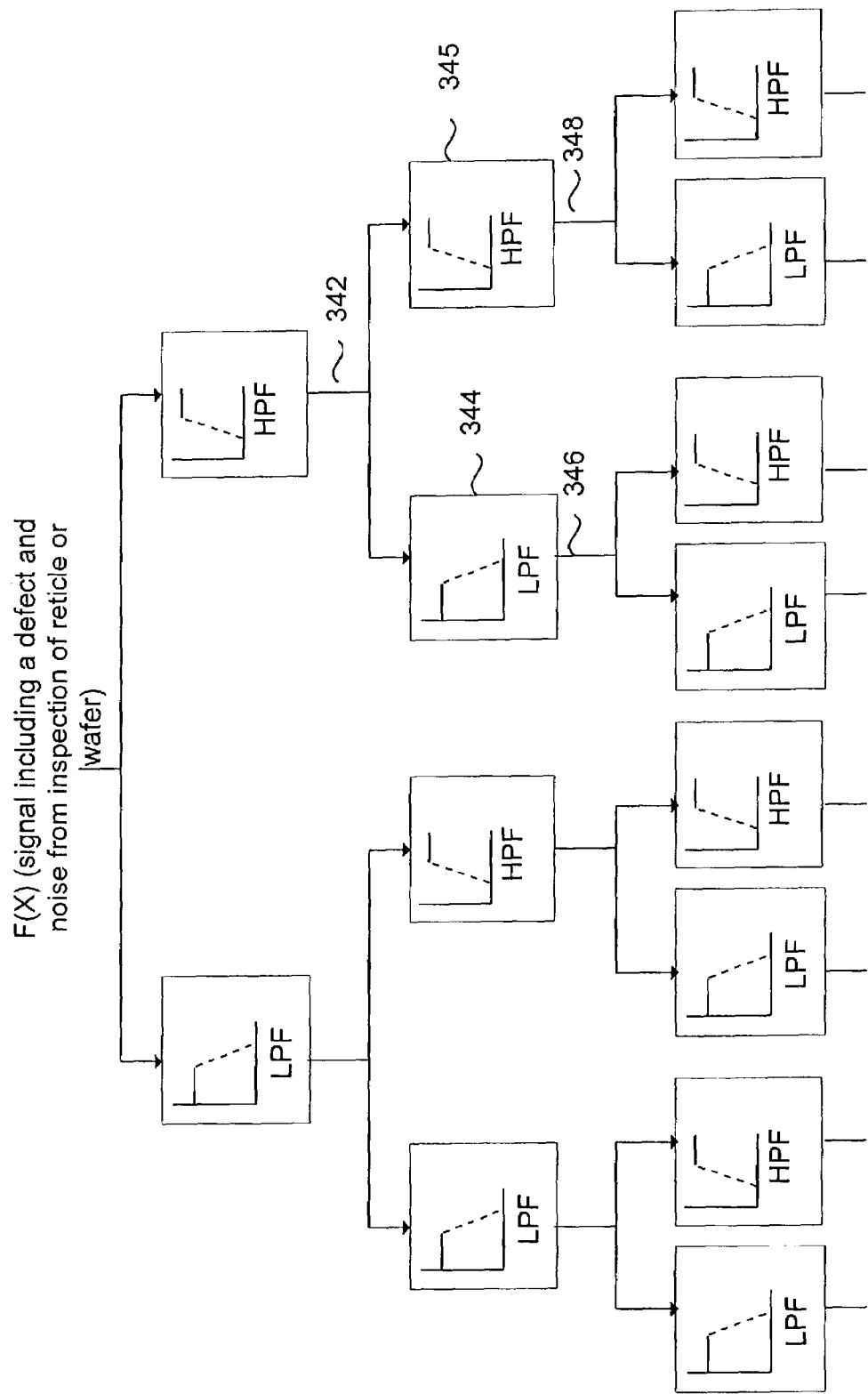
FIG. 3C is a diagrammatic representation illustrating the creation of scaling functions in accordance with another embodiment of the present invention.

FIG. 3C is a diagrammatic representation illustrating the decomposition of an input signal F(x) into several spectral bands according to another embodiment. In this alternate wavelet decomposition, selected bands in the original signal may have a higher resolution, in accordance with the anticipated location of sample defects. In similar fashion to the decomposition illustrated in FIG. 3A, the input signal F(x) is decomposed using a low pass and high pass filter. The high pass filter output 342 is directed to another stage of filtering, the stage comprising a combination of a low pass filter 344 and a high pass filter 345. Each of these filter outputs (346,348) are in turn subjected to a low pass and a high pass filter to produce wavelets. Thus, the input signal F(x) may be filtered to produce multiresolution wavelets, each of the frequency bands corresponding to the wavelet level having resolution in frequency (scale) and time (space) equivalent to other wavelet levels. In another embodiment, only selected frequency bands in the decomposition tree 350 are subjected to further filtering to increase the resolution. For example, in reference to the dyadic levels illustrated in FIG. 3A, the output from high pass filter 304 may be further filtered to produce two wavelet levels instead of one wavelet level comprising the level 2 coefficients. This example is illustrative and not intended to be limiting.

Figure 4A:
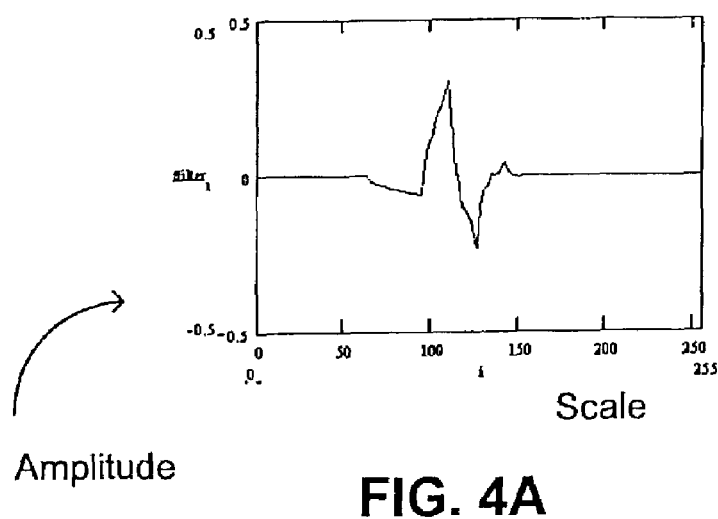
FIG. 4A is a diagrammatic representation of a wavelet basis function used in the wavelet filtering illustrated in FIGS. 4B-4G.

FIG. 4A is a diagrammatic representation of the wavelet basis function used in the wavelet filtering illustrated in FIGS. 4B-4G. Shown is a Daubechies 4 wavelet. The wavelet is irregular in shape and compactly supported. These properties make wavelets in general, and this wavelet in particular, an ideal tool for analyzing signals of a non-stationary nature on wafers or other samples. Defects on wafers, reticles, or photomasks are typically embedded in patterns that are non-stationary. The irregular shape of the wavelet permits analysis of signals having sharp changes (i.e., discontinuities) and the compact support enables the features of the input signal to be localized in time. Use of the Daubechies 4 wavelet is intended to be illustrative and not limiting. Other wavelet basis functions are suitable for use with the present invention and include but are not limited to the Haar basis function and the Gabor basis function.

Figure 4B:
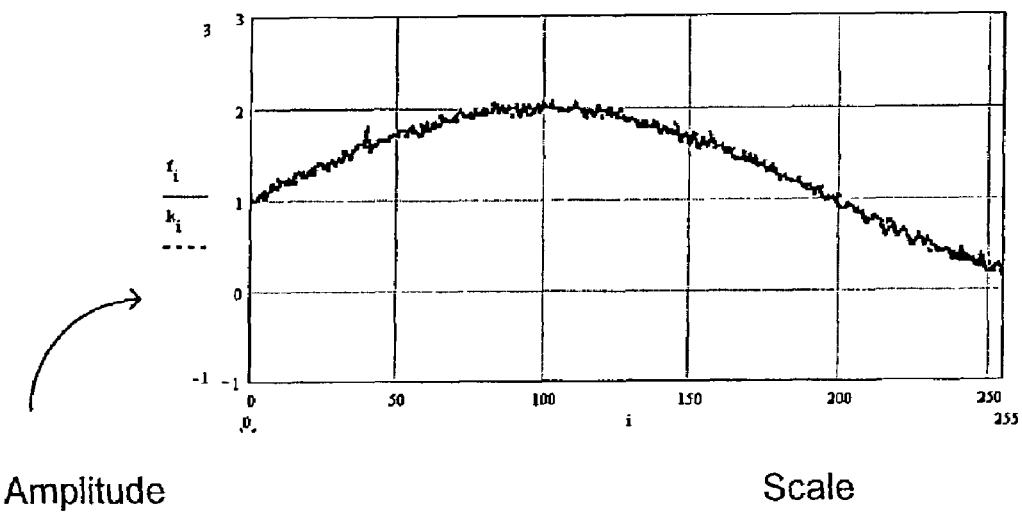
FIGS. 4B-4G are diagrammatic representations illustrating stages in wavelet filtering in accordance with one embodiment of the present invention.
Figure 4C:
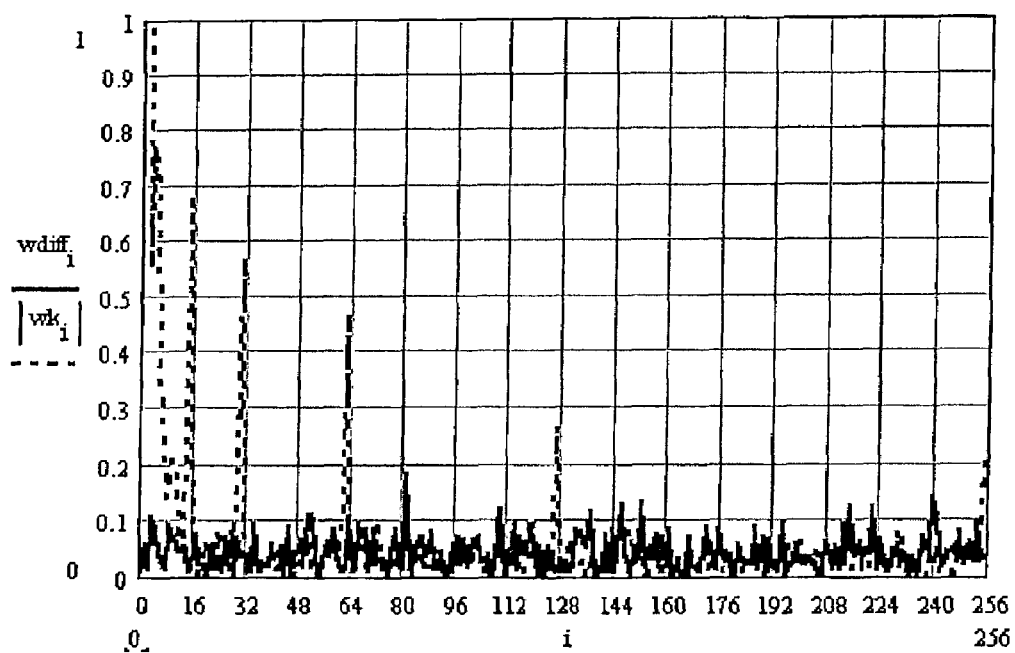

FIGS. 4B-4G are diagrammatic representations illustrating stages of wavelet filtering in accordance with one embodiment of the present invention. FIGS. 4B-4C illustrates the decomposition of the original signal into dyadic blocks through shifting and scaling based on powers of two.

Figure 4D:
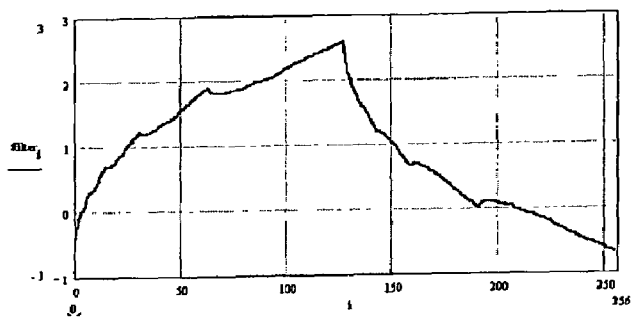
Figure 4E:
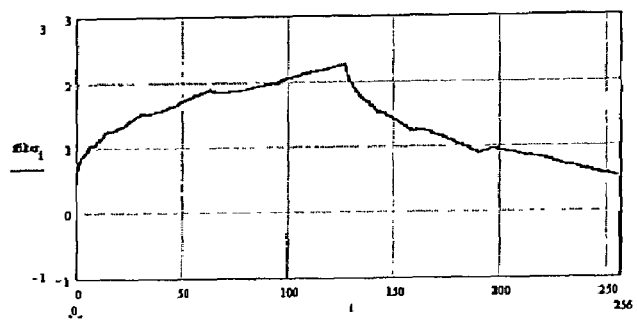
Figure 4F:
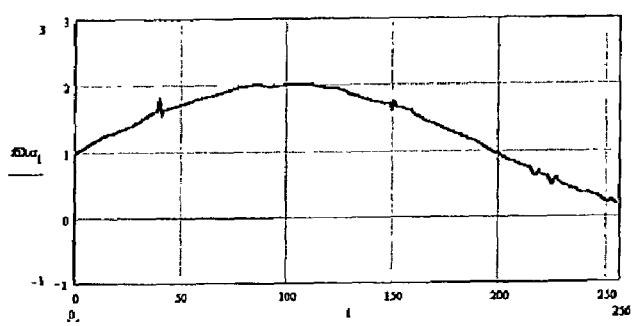
Figure 4G:
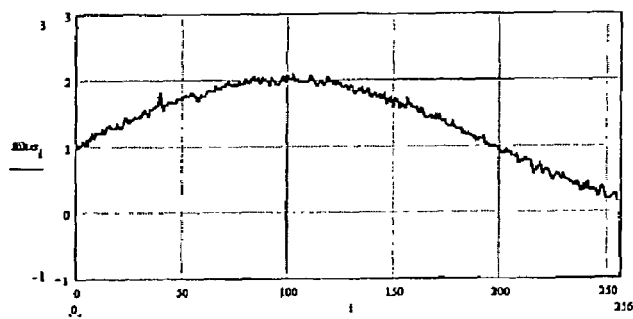

FIG. 4B illustrates a sample normalized input signal before wavelet processing. As illustrated in FIG. 4C, the input signal is transformed using wavelet basis functions. In this embodiment, scaling and shifting process using the discrete wavelet transform produce the time-scale function relating the wavelets correlated to the signal as shown in FIG. 4C. As a result of the translation and dilation (scaling) operations, the wavelet coefficients are produced. These coefficients, assigned in groups to a wavelet coefficient level representing a frequency band of the original image, represent the correlation between the wavelet and a localized section of the signal. FIGS. 4D-4G illustrate signals reconstructed using subsets of the coefficients decomposed from the original signal. In FIG. 4D, only those coefficients having a magnitude greater than 20 are depicted, representing a coarse analysis of the original signal and providing relatively poor resolution. FIGS. 4E-4G represent the reconstruction of the original signal based on increasing the number of coefficients, thus increasing resolution for the reconstructed signal. For example, FIG. 4E represents the reconstruction of the signal using the coefficients of the discrete wavelet transform having magnitudes greater than 5 and FIG. 4F with coefficient magnitudes having magnitudes greater than 0.1. FIG. 4G represents the reconstruction of the signal using all of the coefficients (magnitudes greater than 0.01) of the discrete wavelet transform. As shown, the reconstructed signal provides good matching with the original signal before decomposition. In comparing FIG. 4F with 4G, it can be seen that true defects are more easily ascertained in FIG. 4F than from the reconstructed signal illustrated in FIG. 4G, where reconstruction is based on all coefficients and noise obscures the real defect signals. Thus, in one embodiment of the present invention, proper selection of coefficients will enable an enhanced signal which more facilitates distinguishing between true defects and false defects or noise. For example, FIG. 4G illustrates much of the noise present in the original signal, while FIG. 4F illustrates a minimal amount of noise present.

Figure 5A:
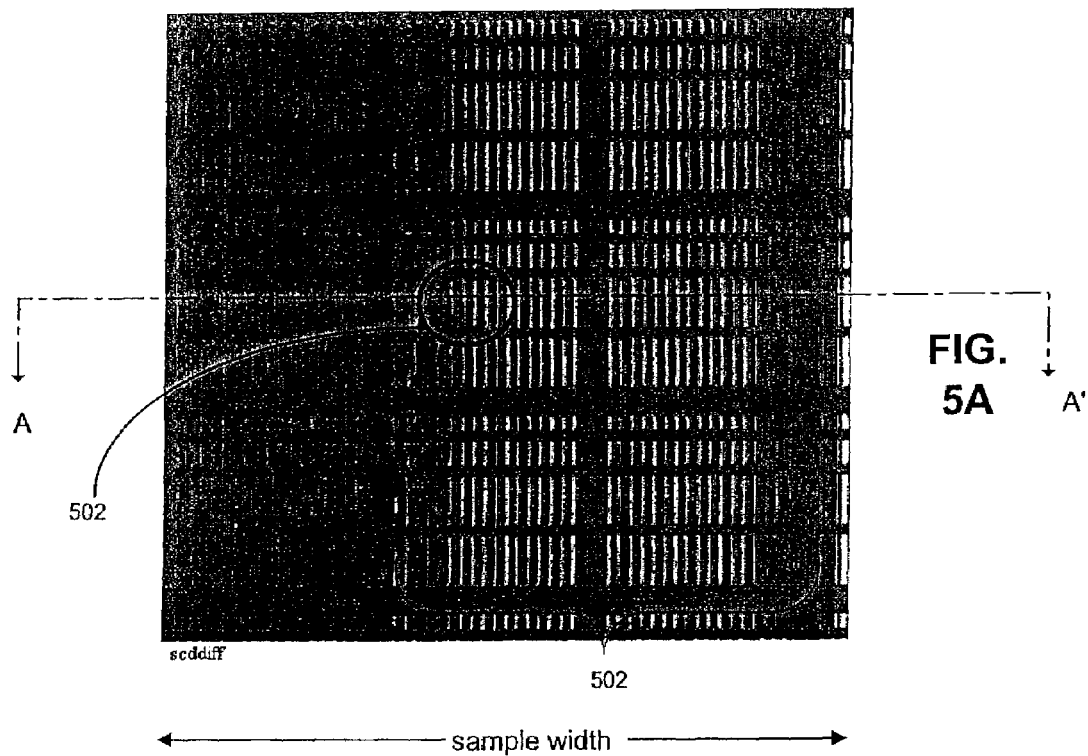
FIGS. 5A-5E illustrate the effects of filtering in accordance with one embodiment of the present invention.
Figure 5B:
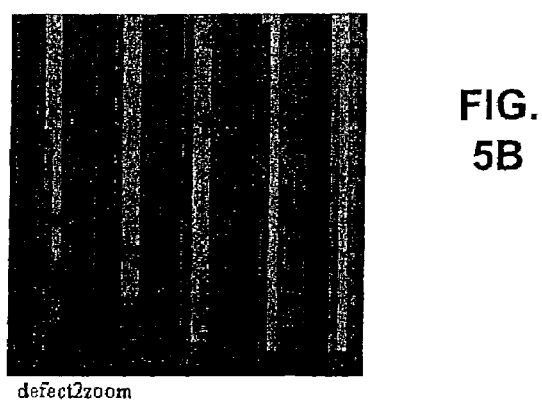
Figure 5C:
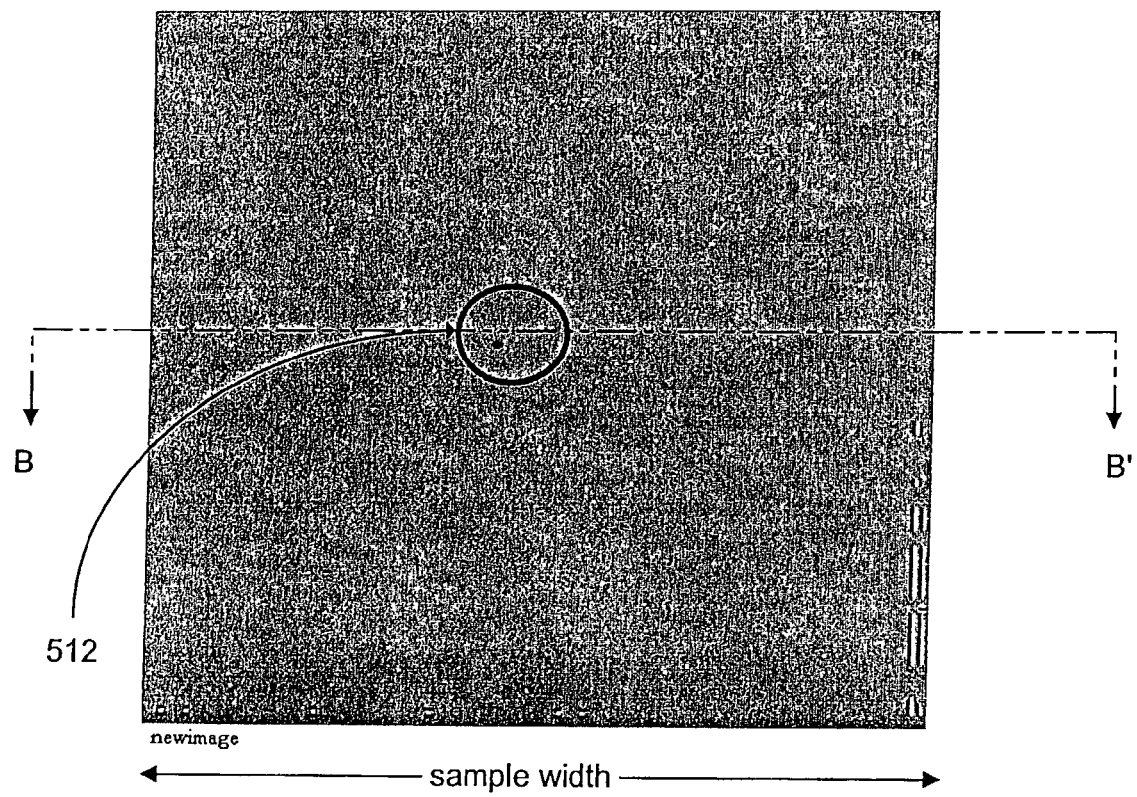
Figure 5D:
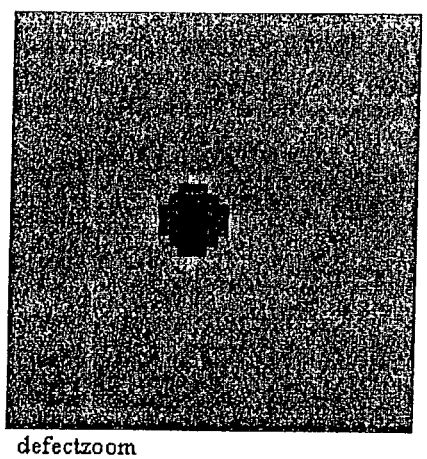

FIG. 5A illustrates a standard (aligned) difference image. As can be seen, defect 502 is difficult to distinguish from pattern noise. FIG. 5B illustrates an enlarged image of defect 502. FIG. 5C illustrates a wavelet transformed, filtered, and inverse transformed image obtained using one embodiment of the methods of the present invention. Defect 512 is more readily distinguishable in comparison to a conventional difference image, as further illustrated in FIG. 5D, an enlarged image of the defect.

Figure 5E:
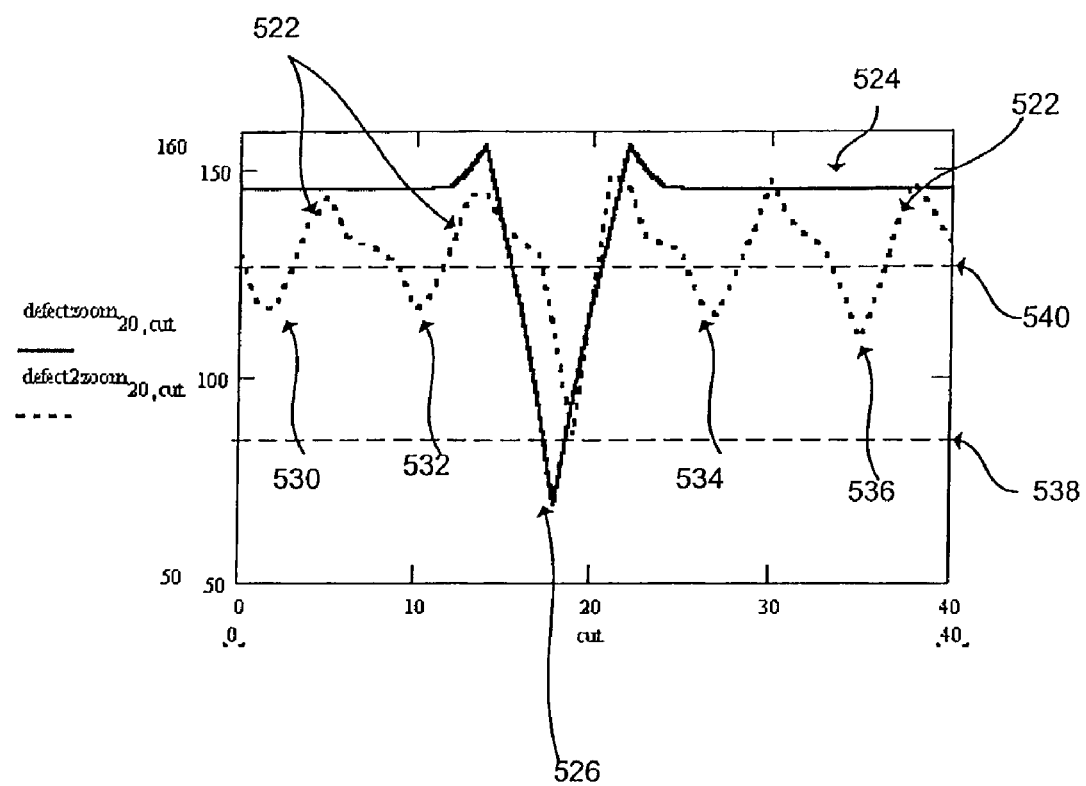

FIG. 5E illustrates a slice of the signal image taken along section A-A' and B-B'. Line 522 represents the one-dimensional signal through section A-A' (i.e., the conventional difference image). Line 524 represents a one-dimensional signal through slice B-B' (i.e., the wavelet transformed, filtered, and inverse transformed image). The defect at point 526 may be more readily identified in the wavelet-processed signal (line 524) as compared to the conventional difference signal (line 522). For example, in one embodiment and as illustrated, coefficients above and below a given range are set to zero. In accordance with another embodiment, a properly selected threshold, such as at threshold line 538, may suppress all of the pattern noise, such as shown along line 522 at points 530, 532, 534, and 536. If the magnitude of the threshold is set too high, real defects may be suppressed. Alternately if a lower threshold such as line 540 is selected, pattern defects will show up as well as real defects. Thus a threshold set at this level will still produce numerous false defects as well as including the real defects. In accordance with another embodiment, selecting a threshold may be performed on both the inverse transformed (reconstructed) image and in the filtering operation performed on the wavelet levels. In yet another embodiment, selecting a threshold takes place only on the coefficients of the wavelet levels.

The invention may be used with any suitable inspection system. FIG. 6 is a simplified block diagram of an optical inspection system 610 that may be used to implement embodiments of the present invention. The optical inspection system 610 is arranged for inspecting a surface 611 of a substrate 612. The dimensions of various components are exaggerated to better illustrate the optical components of this embodiment. As shown, the optical inspection system 610 includes an optical assembly 614, a stage 616, and a control system 617. The optical assembly 614 generally includes at least a first optical arrangement 622 and a second optical arrangement 624. In general terms, the first optical arrangement 622 generates a illumination beam incident on the substrate, and the second optical arrangement 624 detects a illumination beam emanating from the sample as a result of the incident illumination beam. The first and second optical arrangement may be arranged in suitable manner in relation to each other. For example, the second optical arrangement 624 and the first optical arrangement 622 may both be arranged over the substrate surface 611 so that reflected illumination beam resulting from incident illumination beam generated by the first optical arrangement 622 may be detected by the second optical arrangement 624. Several embodiments of the optical assembly 614 altered to implement the present invention are described further below with reference to FIG. 6.

In the illustrated embodiment, the first optical arrangement 622 is arranged for generating an illumination spot (not shown) on the surface 611 of the substrate 612. On the other hand, the second optical arrangement 624 is arranged for collecting reflected light that is produced by the illumination spot on the surface 611 of the substrate 612.

To elaborate further, the first optical arrangement 622 includes at least a light source 626 for emitting a light beam 634 and a first set of optical elements 628. The first set of optical elements 28 may be arranged to provide one or more optical capabilities including, but not limited to, directing the light beam 634 towards a beam splitter (not shown) and through an objective lens (not shown) to intersect with the surface 611 of the substrate 612. A portion of the incident beam 634 is reflected by the beam splitter and becomes incident beam 636 which is focused by the objective to a illumination spot (not shown in FIG. 6) on the surface 611 of the substrate 612.

Furthermore, the second optical arrangement 624 includes at least a second set of optical elements 630 and an imaging device 632. The second set of optical elements 630 are in the path of a collected light beam 640, which is formed after the incident light beam 636 intersect with the surface 611 of the substrate 612. The collected light beam 640 may result from reflected light beam 641 that is reflected off the surface 611 of the substrate 612. A portion of the reflected beam 641 passes by beam splitter 637 and becomes collected beam 640. The second set of optical elements 630 are adapted for collecting the collected light beam 640 and for forming an image of a portion of surface 611 of substrate 612 on the imaging device 632. The imaging device 632 is arranged for detecting the light intensity distribution of the collected light beam 640, and more particularly for detecting distribution in the intensity of light caused by the intersection of the incident light beam with the substrate. The imaging device 632 is arranged for detecting the light intensity distribution of the image and for generating signals based on the detected light.

With regards to the stage 616, the stage 616 is arranged for moving the substrate 612 within a single plane (e.g., x & y directions) and relative to incident beam 636, so that all or any selected part of the substrate surface 611 may be inspected by the illumination spot.

The control system 617 generally includes a control computer 618 and an electronic subsystem 619. Although not shown, the control system 617 may also include a keyboard for accepting operator inputs, a monitor for providing visual displays of the inspected substrate (e.g., defects), a database for storing reference information, and a recorder for recording the location of defects. As shown, the control computer 618 is coupled to the electronic subsystem 619. The electronic subsystem 619 is coupled to various components of the optical inspection system 610, and more particularly to the stage 616 and the optical assembly 614 including the first optical arrangement 622 and the second optical arrangement 624. Hardware and/or software for performing the wavelet transformation, filtering, and inverse transformation may in one embodiment be contained in the electronics system 619. In another embodiment, the wavelet transformation, inverse transformation, and digital filtering may be performed within computer 618 when loaded with appropriate computer media containing the instructions for performing the techniques of this invention. The control system shown is intended to be illustrative and not limiting. The wavelet transformation, inverse transformation, digital filtering, and signal comparison procedures may be implemented by any suitable combination of hardware and/or software.

The control computer 618 may be arranged to act as an operator console and master controller of the system 610. By way of example, commands may be issued to and status may be monitored from all other subsystems so as to facilitate completion of operator assigned tasks. Additionally, the electronics subsystem 619 may also be configured to interpret and execute the commands issued by control computer 618. The configuration may include capabilities for, but not limited to, digitizing the input from imaging devices, compensating these readings for variations in the incident light intensity, constructing a virtual image of the substrate surface based on the detected signals, detecting defects in the image and transferring the defect data to the control computer 618, accumulating the output of the interferometers used to track the stage 616, providing the drive for linear motors that move the stage 616 or components of the optical assembly 14, and monitoring sensors which indicate status. Control systems and stages are well known in the art and for the sake of brevity will not be discussed in greater detail. A representative stage, as well as a representative controller, may be found in U.S. Pat. No. 5,563,702, which is herein incorporated by reference. It should be understood, however, that this is not a limitation and that other suitable stages and control systems may be used.

In most of the defect detection operations a comparison is made between two images. By way of example, the comparison may be implemented by the electronic subsystem 619 of FIG. 1. Broadly speaking, the imaging device 632 generates images, which are based on the measured light intensity distribution, and sends them to the electronic subsystem 619. The electronic subsystem 619, after receiving the images, compares the target images with reference images, which are either stored in a database or determined in a current or previous measurement.

In die-to-die inspection mode, two areas of the substrate having identical features are compared to each other and any substantial discrepancy is flagged as a defect. In the die-to-database inspection mode, a defect is detected by comparing the die under test with corresponding graphics information obtained from a computer aided database system from which the die was derived.

Suitable computer systems for use in implementing and controlling the methods in the present invention (e.g., controlling the settings of the various scanning apparatus components, storing and retrieving a baseline image of the wafer, storing a test image of the wafer, comparing the test image with one or more baseline images, storing the line-shortening measurements and statistical information during such comparisons, etc.) may be obtained from various vendors (e.g., Silicon Graphics of Mountain View, Calif. or Sun Microsystems of Sunnyvale, Calif.) or custom built by a wafer inspection system vendor, such as KLA-Tencor.

The term "electronic representation" as used herein covers any machine readable representation. Typically, such representations are stored on magnetic, electronic, or optically readable media. The content of such representations may be transmitted as electrical signals, magnetic signals, electromagnetic signals, optical signals, etc.

Preferably, an optical or other inspection system is integrated with a computer system which implements many of the method steps of this invention. Such composite system preferably includes at least (a) a baseline image (preferably compacted) stored in memory, (b) an imaging system arranged to generate an optical image of the wafer, and (c) a processing unit configured to compare the baseline and current test images and thereby identify defects, as well as compute according to the mathematical models described herein focus and exposure responses corresponding to optical measurements as well as store various statistical information. At a minimum, the imaging system will usually include (i) a source of illumination oriented to direct radiation onto a specified location of the wafer; and (ii) one or more detectors oriented to detect an image of the wafer from the source which has been scattered by the wafer. The imaging system may also include a scanning means.

Although the foregoing invention has been described in some detail for purposes of clarity of understanding, it will be apparent that certain changes and modifications may be practiced within the scope of the appended claims. It should be noted that there are many alternative ways of implementing both the process and inspection system of the present invention. For example, performing a wavelet transform, digital filtering, and performing an inverse transform may be performed in any suitable combination of hardware and software. Additionally, the hardware and/or software may be configured to implement any suitable wavelet transformation using wavelet basis functions suitably matched to the defect types anticipated. Accordingly, the present embodiments are to be considered as illustrative and not restrictive, and the invention is not to be limited to the details given herein, but may be modified within the scope and equivalents of the appended claims.

What is claimed is:

1. A method of detecting a defect in a reticle or wafer, the method comprising:

obtaining a first image of a portion of the wafer or reticle and a second image of a portion of a same or different wafer or reticle or rendered from a design database file corresponding to a portion of a same or different wafer or reticle;

obtaining a wavelet transform of a difference between the first image and the second image;

filtering the wavelet transformed image of the difference between the first image and the second image so as to substantially eliminate portions of the wavelet transformed image that contain pattern and/or random noise and so as to substantially retain portions of the wavelet transformed image that correspond to real defect differences between the wafer or reticle portions;

producing an inverse wavelet transform of the filtered image; and determining whether there is a defect in the first or second image based on the inverse wavelet transformed image whereby it is determined that there is a defect when the inverse wavelet transformed image corresponds to a real defect difference between the reticle or wafer portions.

2. The method described in claim 1 wherein filtering the transformed image comprises identifying a portion of the transformed image coefficients within a predefined range as noise and modifying the values of the identified portion of the transformed image coefficients.

3. The method described in claim 2 wherein modifying values of the identified portion of the transformed image coefficients comprises setting the values of the coefficients to zero.

4. The method described in claim 2 wherein the identified portion of the transformed image coefficients are each greater than a specified threshold.

5. The method described in claim 2 wherein the identified portion of the transformed image coefficients are each less than a specified threshold.

6. The method described in claim 2 wherein identifying a portion of the transformed image coefficients within a predefined range and modifying the values of the identified portion of the transformed image coefficients is applied to only selected wavelet levels, wherein each wavelet level includes transformed image coefficients within a specific range.

7. The method described in claim 6 wherein the coefficients magnitudes in the wavelet levels which are not selected are uniformly reduced.

8. A semiconductor mask, reticle, or wafer inspection system for identifying defects, the system comprising:

an image generating source for generating an image from masks, reticles, or wafers; and a processor configured to perform the following steps:

obtaining a first image of a portion of the wafer or reticle and a second image of a portion of a same or different wafer or reticle or rendered from a design database file corresponding to a portion of a same or different wafer or reticle;

obtaining a wavelet transform of a difference between the first image and the second image;

filtering the wavelet transformed image of the difference between the first image and the second image so as to substantially eliminate portions of the wavelet transformed image that contain pattern and/or random noise and so as to substantially retain portions of the wavelet transformed image that correspond to real defect differences between the wafer or reticle portions;

producing an inverse wavelet transform of the filtered image; and determining whether there is a defect in the first or second image based on the inverse wavelet transformed image whereby it is determined that there is a defect when the inverse wavelet transformed image corresponds to a real defect difference between the reticle or wafer portions.

9. A computer program product comprising:

a computer readable medium having computer program instructions stored within the at least one computer readable product configured to cause a device to be programmed to perform the steps of:

obtaining a first image of a portion of the wafer or reticle and a second image of a portion of a same or different wafer or reticle or rendered from a design database file corresponding to a portion of a same or different wafer or reticle;

obtaining a wavelet transform of a difference between the first image and the second image;

filtering the wavelet transformed image of the difference between the first image and the second image so as to substantially eliminate portions of the wavelet transformed image that contain pattern and/or random noise and so as to substantially retain portions of the wavelet transformed image that correspond to real defect differences between the wafer or reticle portions;

producing an inverse wavelet transform of the filtered image; and determining whether there is a defect in the first or second image based on the inverse wavelet transformed image whereby it is determined that there is a defect when the inverse wavelet transformed image corresponds to a real defect difference between the reticle or wafer portions.

* * * * *